(12) United States Patent
Bhatt et al.

(10) Patent No.: US 10,970,640 B2
(45) Date of Patent: *Apr. 6, 2021

(54) DETERMINING A RISK SCORE USING A PREDICTIVE MODEL AND MEDICAL MODEL DATA

(71) Applicant: International Business Machines Corporation, Armonk, NY (US)

(72) Inventors: Dhruv A. Bhatt, Indian Trail, NC (US); Kristin E. McNeil, Charlotte, NC (US); Nitaben A. Patel, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 312 days.

This patent is subject to a terminal disclaimer.

(21) Appl. No.: 14/886,340

(22) Filed: Oct. 19, 2015

(65) Prior Publication Data

US 2016/0321423 A1    Nov. 3, 2016

Related U.S. Application Data

(63) Continuation of application No. 14/698,012, filed on Apr. 28, 2015.

(51) Int. Cl.
*G06N 5/02* (2006.01)
*G06F 40/10* (2020.01)
(Continued)

(52) U.S. Cl.
CPC ............. *G06N 5/025* (2013.01); *G06F 40/10* (2020.01); *G06F 40/169* (2020.01); *G06F 40/20* (2020.01);
(Continued)

(58) Field of Classification Search
None
See application file for complete search history.

(56) References Cited

U.S. PATENT DOCUMENTS 6,236,878 B1    5/2001   Taylor et al.
7,058,582 B2    6/2006   Powell
(Continued)

FOREIGN PATENT DOCUMENTS

WO        2014036173 A1    3/2014

OTHER PUBLICATIONS

Lehman, L-W, et al. "Risk Stratification of ICU Patients Using Topic Models Inferred from Unstructured Progress Notes". AMIA Annu Symp Proc. 2012; 2012: 505-511. (Year: 2012).*

(Continued)

*Primary Examiner* — Kamran Afshar
*Assistant Examiner* — Benjamin J Buss
(74) *Attorney, Agent, or Firm* — Konrad Raynes Davda & Victor LLP; Janaki K. Davda

(57) ABSTRACT

Methods for text analysis of medical study data to extract predictive data. Natural language processing is performed on a document in a collection of documents to determine whether the document contains medical model data. In response to determining that the document contains medical model data, content relating to the medical model data in the document is annotated. A first medical model is generated based on the annotations for the identified medical model data and a certainty threshold In response to the certainty threshold meeting a user setting, the first medical model is added to a predictive model for determining a risk score, based on the analyzed data.

3 Claims, 2 Drawing Sheets

(51) Int. Cl.
| | |
|---|---|
| G16H 50/30 | (2018.01) |
| G16H 50/70 | (2018.01) |
| G16H 15/00 | (2018.01) |
| G06F 40/169 | (2020.01) |
| G06F 40/20 | (2020.01) |

(52) U.S. Cl.
CPC ............. *G16H 15/00* (2018.01); *G16H 50/30* (2018.01); *G16H 50/70* (2018.01)

(56) References Cited

U.S. PATENT DOCUMENTS

| | | | |
|---|---|---|---|
| 7,913,224 | B2 | 3/2011 | Nissen et al. |
| 9,536,522 | B1* | 1/2017 | Hall ...................... G10L 15/063 |
| 10,452,981 | B1 | 10/2019 | Christie, IV et al. |
| 2004/0243545 | A1* | 12/2004 | Boone ..................... G16H 10/60 |
| 2005/0027664 | A1* | 2/2005 | Johnson .............. G06F 17/2827 706/12 |
| 2005/0071217 | A1* | 3/2005 | Hoogs ................ G06Q 10/0635 705/7.28 |
| 2010/0023319 | A1* | 1/2010 | Bikel ..................... G06F 17/241 704/9 |
| 2010/0306281 | A1 | 12/2010 | Williamson |
| 2011/0040576 | A1 | 2/2011 | Madan et al. |
| 2012/0109858 | A1 | 5/2012 | Makadia et al. |
| 2012/0239435 | A1* | 9/2012 | Ennett ..................... G16H 15/00 705/3 |
| 2013/0006912 | A1* | 1/2013 | Christie, IV .......... G06F 19/324 706/47 |
| 2013/0138439 | A1* | 5/2013 | Marcus ................... G10L 15/22 704/240 |
| 2013/0231949 | A1* | 9/2013 | Baronov ................. G06F 19/00 705/2 |
| 2014/0012866 | A1* | 1/2014 | Bowman ............. G06F 17/2705 707/755 |
| 2014/0088989 | A1 | 3/2014 | Krishnapuram et al. |
| 2014/0122126 | A1* | 5/2014 | Riskin ..................... G16H 50/30 705/3 |
| 2014/0188459 | A1 | 7/2014 | Fink et al. |
| 2014/0280066 | A1* | 9/2014 | Petschulat ......... G06F 17/30539 707/722 |
| 2014/0314765 | A1 | 10/2014 | DePinho et al. |
| 2014/0330586 | A1* | 11/2014 | Riskin ................. G06F 17/2765 705/3 |
| 2014/0359421 | A1 | 12/2014 | Allen et al. |
| 2015/0032442 | A1* | 1/2015 | Marcus ................. G06F 17/271 704/9 |
| 2015/0039344 | A1* | 2/2015 | Kinney ................. G06F 19/328 705/3 |
| 2015/0066539 | A1* | 3/2015 | Sheffer .................. G06Q 50/22 705/3 |
| 2015/0134362 | A1 | 5/2015 | Schneider et al. |
| 2015/0142472 | A1 | 5/2015 | Schulte et al. |
| 2015/0269332 | A1 | 9/2015 | Schneider et al. |
| 2015/0356198 | A1* | 12/2015 | D'Souza ................. G06F 16/84 705/2 |
| 2016/0180038 | A1 | 6/2016 | Clark et al. |
| 2016/0189303 | A1 | 6/2016 | Fuchs |
| 2016/0321426 | A1 | 11/2016 | Bhatt et al. |
| 2017/0154374 | A1* | 6/2017 | Iglesias .............. G06Q 30/0629 |

OTHER PUBLICATIONS

Lussier, Y., et al. (2006). PhenoGO: assigning phenotypic context to gene ontology annotations with natural language processing. In Biocomputing 2006 (pp. 64-75). DOI:10.1142/9789812701626_0007 (Year: 2006).*

Stanfill, M.H. et al. "A systematic literature review of automated clinical coding and classification systems". J Am Med Inform Assoc 2010;17:646e651. doi:10.1136/jamia.2009.001024 (Year: 2010).*

Liao, K.P. et al. "Electronic Medical Records for Discovery Research in Rheumatoid Arthritis". Arthritis Care & Research. vol. 62, No. 8, Aug. 2010, pp. 1120-1127DOI 10.1002/acr.20184 (Year: 2010).*

Mangiameli, P., et al. (2004). "Model selection for medical diagnosis decision support systems". Decision Support Systems, 36(3), 247-259. (Year: 2004).*

Lo, H.-Y. et al. (2008). "Learning to improve area-under-FROC for imbalanced medical data classification using an ensemble method." ACM SIGKDD Explorations Newsletter 10.2 (2008): 43-46. (Year: 2008).*

Wu, J.A. et al (2012). "Extracting Relevant Information from Clinical Records: Towards Modeling the Evolution of Intracranial Aneurysms." AMIA. 2012. (Year: 2012).*

Pakhomov, S. et a. (2005). "High throughput modularized NLP system for clinical text." Proceedings of the ACL 2005 on Interactive poster and demonstration sessions. Association for Computational Linguistics, 2005. (Year: 2005).*

Savova, G., et al. (2008). "UIMA-based clinical information extraction system." Towards enhanced interoperability for large HLT systems: UIMA for NLP 39 (2008). (Year: 2008).*

Demner-Fushman, D. (2009). "What can natural language processing do for clinical decision support?." Journal of biomedical informatics 42.5 (2009): 760-772. (Year: 2009).*

Kiritchenko, S, et al. (2010). "ExaCT: automatic extraction of clinical trial characteristics from journal publications." BMC medical informatics and decision making 10.1 (2010): 56. (Year: 2010).*

Zhang, Yi. (Jul. 2010). "Multi-task active learning with output constraints." Twenty-Fourth AAAI Conference on Artificial Intelligence. 2010. (Year: 2010).*

Muslea, I. (Jul. 1999). "Extraction patterns for information extraction tasks: A survey." The AAAI-99 workshop on machine learning for information extraction. vol. 2. No. 2. 1999. (Year: 1999).*

Anonymously; "Method to extract simple and compound terms from text corpuses (without performing full semantic analysis)"; An IP.com Prior Art Database Technical Disclosure; http://ip.com/IPCOM/000220204; Jul. 25, 2012. 6 pp.

Barbar, S., et al.; "A risk assessment model for the identification of hospitalized medical patients at risk for venousthromboembolism: the Padua Prediction Score."; Journal of Thrombosis and Haemostasis. Nov. 2010;8(11):2450-7. doi: 10.1111/j.1538-7836.2010.04044.x. 3 pp, Abstract Only.

Billings, J., et al.; "Development of a predictive model to identify inpatients at risk of re-admission within 30 daysof discharge (PARR-30)"; BMJ Open 2012;2:e001667 doi:10.1136/bmjopen-2012-001667. 9 pp.

Inouye, S., et al.; "A Predictive Model for Delirium in Hospitalized Elderly Medical Patients Based on Admission Characteristics"; Annals of Internal Medicine. 1993;119(6):474-481. 3 pp, Abstract Only.

Kannel, et al.; Framingham Heart Study: Congestive Heart Failure Risk; <https://www.framinghamheartstudy.org/risk-functions/congestive-heart-failure/>. Downloaded Aug. 5, 2014. 6 pp.

Kumar, N. et al.; "Machine Learning based Predictive Model for Analyzing the Sentiments in Short Text"; An IP.com Prior Art Database Technical Disclosure; http://ip.com/IPCOM/000239081; Oct. 10, 2014. 10 pp.

Schnabel, RB, et al.; "Framingham Heart Study AF score (10-year risk)"; <http://www.framinghamheartstudy.org/risk-functions/atrial-fibrillation/10-year-risk.php>. Downloaded Dec. 23, 2014. 3 pp.

Shen, T. et al.; "Active volume models for medical image segmentation"; IEEE Transactions on Medical Imaging, vol. 30, No. 3, pp. 774-791; Mar. 2011. 18 pp.

Tangri, N., et al.; "Risk prediction models for patients with chronic kidney disease: a systematic review."; Annals of Internal Medicine. Apr. 16, 2013;158(8):596-603. 3 pp, Abstract Only.

Wilson, et al.; Diabetes Risk; Framingham Heart Study; <http://www.framinghamheartstudy.org/risk-functions/diabetes/index.php> Downloaded Dec. 23, 2014. 3 pp.

List of IBM Patents or Patent Applications Treated as Related.

Kansagara, D., et al.; "Risk Prediction Models for Hospital Readmission"; JAMA. 2011;306(15):1688-1698. doi:10.1001/jama.2011.1515. 21 pp.

Antal, P. et al. (2004). "Using literature and data to learn Bayesian networks as clinical models of ovarian tumors". ArtificialIntelligence in Medicine 30 (2004) 257-281. (Year: 2004).

(56) References Cited

OTHER PUBLICATIONS

LePendu, P. et al. (2011). "Annotation analysis for testing drug safety signals using unstructured clinical notes". Journal of Biomedical Semantics 2012, 3(Suppl 1):S5. From Bio-Ontologies 2011. (Year: 2011).
Office Action 1 for U.S. Appl. No. 14/698,012, 16 pp., dated Oct. 20, 2017. [57.494 (OA1)].
Response to Office Action 1 for U.S. Appl. No. 14/698,012, 9 pp., dated Jan. 22, 2018. [57.494 (ROA1)].
Final Office Action 1 for U.S. Appl. No. 14/698,012, 18 pp., dated Jun. 4, 2018. [57.494 (FOA1)].
Response to Final Office Action 1 for U.S. Appl. No. 14/698,012, 8 pp., dated Oct. 4, 2018. [57.494 (RFOA1)].
Office Action 3 for U.S. Appl. No. 14/698,012, 14 pp., dated Dec. 13, 2018. [57.494 (OA3)].
Response to Office Action 3 for U.S. Appl. No. 14/698,012, 7 pp., dated Mar. 13, 2019. [57.494 (ROA3)].
Final Office Action 2 for U.S. Appl. No. 14/698,012, 18 pp., dated Jul. 12, 2019. [57.494 (FOA2)].
Response to Final Office Action 2 for U.S. Appl. No. 14/698,012, 7 pp., dated Dec. 12, 2019. [57.494 (RFOA2)].
Office Action 5 for U.S. Appl. No. 14/698,012, 15 pp., dated Jan. 15, 2020. [57.494 (OA5)].
Response to Office Action 5 for U.S. Appl. No. 14/698,012, 10 pp., dated Apr. 15, 2020. [57.494 (ROA5)].
Final Office Action 3 for U.S. Appl. No. 14/698,012, 27 pp., dated Jul. 31, 2020. [57.494 (FOA3)].
Response to Final Office Action 3 for U.S. Appl. No. 14/698,012, 14 pp., dated Oct. 14, 2020. [57.494 (RFOA3)].
Notice of Allowance 1 for U.S. Appl. No. 14/698,012, 11 pp., dated Nov. 18, 2020.

* cited by examiner

DETERMINING A RISK SCORE USING A PREDICTIVE MODEL AND MEDICAL MODEL DATA

BACKGROUND

The present invention relates to text analytics, and more specifically, to using text analytics of medical study data. In the healthcare industry, there are a vast number of new studies being published everyday. With the current use of the Internet, these studies are accessible electronically to people. However, it is hard to keep up with reading these studies to uncover new pieces of information, especially for medical personnel like doctors and nurses, who are often very busy caring for their patients.

Predictive analytics encompasses a variety of statistical techniques from modeling, machine learning, and data mining that analyze current and historical facts to make predictions about future, or otherwise unknown, events. Predictive analytics can be used to create models that capture relationships among many factors to allow assessment of risk or potential associated with a particular set of conditions. These models can be used to guide decision making in a variety of areas, including healthcare.

Currently, there are a few Medical Models published on the web that could be used for Predictive Analytics Model. Some of these medical models include:

- A Predictive Model for Delirium in Hospitalized Elderly Medical Patients Based on Admission Characteristics (annals.org/article.aspx?articleid=706724)
- A risk assessment model for the identification of hospitalized medical patients at risk for venous thromboembolism: the Padua Prediction Score (www.ncbi.nlm.nih.gov/pubmed/20738765)
- Risk Prediction Models for Hospital Readmission (jama.jamanetwork.com/article.aspx?articleid=1104511)
- Risk prediction models for patients with chronic kidney disease: a systematic review (www.ncbi.nlm.nih.gov/pubmed/23588748)
- Development of a predictive model to identify inpatients at risk of re-admission within 30 days of discharge (PARR-30) (bmjopen.bmj.com/content/2/4/e001667.full)
- Framingham diabetes (www.framinghamheartstudy.org/risk-functions/diabetes/index.php)
- Framingham Heart Study AF Score (10-year risk) (www.framinghamheartstudy.org/risk-functions/atrial-fibrillation/10-year-risk.php)

However, it takes time to find these and convert the logic into a model that can be used with software that can produce predictive models, such as a Statistical Package for the Social Sciences (SPSS) model). Typically, it is necessary to manually create the models based on the logic mentioned in the studies, like the ones referenced above. Thus, there is a need for an improved way of generating predictive models.

SUMMARY

According to one embodiment of the present invention, techniques are described for text analysis of medical study data to extract predictive data. Natural language processing is performed on a document in a collection of documents to determine whether the document contains medical model data. In response to determining that the document contains medical model data, content relating to the medical model data in the document is annotated. A first medical model is generated based on the annotations for the identified medical model data and a certainty threshold In response to the certainty threshold meeting a user setting, the first medical model is added to a predictive model for determining a risk score, based on the analyzed data.

The details of one or more embodiments of the invention are set forth in the accompanying drawings and the description below. Other features and advantages of the invention will be apparent from the description and drawings, and from the claims.

BRIEF DESCRIPTION OF THE SEVERAL VIEWS OF THE DRAWINGS

Like reference symbols in the various drawings indicate like elements.

DETAILED DESCRIPTION

The various embodiments described herein pertain to techniques for performing text analysis on medical study data to extract predictive data from medical studies around a category (for example, that a Chronic Heart Failure (CHF) diagnosis may result in a 50% mortality rate over the next 5 years). Text analysis, in particular natural language processing (NLP), uses dictionaries and rules to annotate content in order to determine whether the content is related to a medical model. If the content is determined to contain medical model information, then the text analysis tool obtains the section of text for the first model. It determines each instruction phrase of the medical model section. Instruction phrases are similar to text analytic rules. One example of an instruction phrase is "if age>70, then risk=3." If there are more instruction phrases in this model's section of text, then they are also determined.

A model generator engine generates the medical model based on the medical model information determined from the text analytics and based on a certainty threshold. Typically, this certainty threshold is configured by a user in some kind of property file or user interface, but it should be realized that there are also many other ways to configure certainty thresholds that are available to those having ordinary skill in the art. If the certainty threshold meets a predefined user setting, then the piece of information is added to the model. Further, if there are more rules identified for this medical model, then they are also added to the model. If there are more sections with medical model information, then those sections of text are also analyzed to determine the model information (as annotations) and another model is generated. As is familiar to those having ordinary skill in the art, an annotation is the resulting value from the identified rule or dictionary. For example, if an AgeIndicator rule is <Age dictionary term> followed by a mathematical symbol followed by a number, then when the text "Age>70" is analyzed, the rule is fired off and generates an AgeIndicator annotation with value Age>70. Annotators and Annotation terms are part of the Unstructured Information Management Architecture (UIMA) framework, which is one possible framework implementation in the various embodiments described herein. The generated predictive model can then be used to determine a risk score based on the analyzed data. Various embodiments will now be described in further detail by way of example and with reference to the figures.

Figure 1:
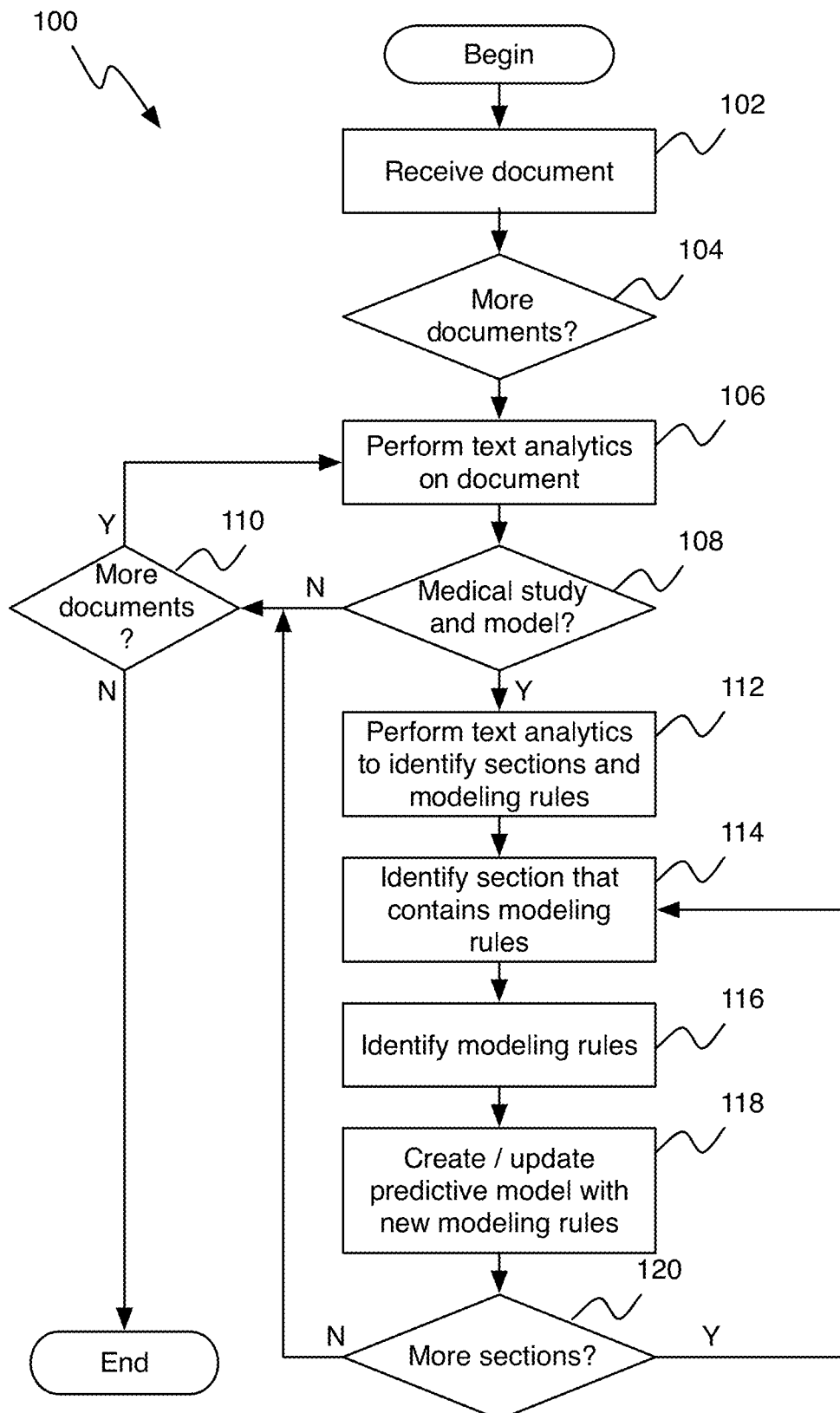
FIG. 1 shows a flowchart for generating a predictive model based on medical model data, in accordance with one embodiment.

FIG. 1 shows a flowchart of a process (100) for generating a predictive model based on medical model data, in accordance with one embodiment. As can be seen in FIG. 1, the process (100) starts by inputting a document into the system (step 102). The document is known to contain medical model information and can be input, for example, by a user uploading the document to the system, or by automatically accessing the document from a database.

Next, it is determined if there are any more documents to be input (step 104). If there are more documents, the system returns to step 102 to obtain the next document. If there are no more documents, the process continues to step 106, where medical study and model parsing rules and dictionaries are used to perform natural language processing on a selected document.

Based on the text annotations generated in step 106, a determination is made as to whether there is a medical study and model present in the selected document (step 108). If it is determined that there is no medical study and model present in the selected document, the process continues to check if there are any more documents available (step 110). If there are more documents available, the process returns to step 106 and continues as outlined above.

If it is determined in step 108 that there is a medical study and model present in the selected document, the text analytics annotations for the determined section and modeling rule are obtained. This is based on section and modeling rule dictionaries and parsing rules (step 112).

Next, the section that contains the sections and modeling rules is identified (step 114) based on the annotations generated in step 112.

Next, the modeling rules that are located within the section are identified (step 116). This identification is based on using the Common Analysis Structure (CAS) Subject of Analysis (SOFA) index values of the UIMA framework for the section and finding the modeling rule annotations that are identified within the annotation index range. SOFA describes a way of storing the information (annotations) in memory to be able to retrieve and work with them. For example, at character 11 there is a first name annotation (Kristin) identified in this line: "My name is Kristin McNeil". The annotation index range is the beginning and end values for the identified phrase for the annotation. For example, in the above "My name is Kristin McNeil" phrase, the begin and end values would be 11 and 17, respectively.

Next, in step 118, a model generator program is used to create/update a predictive model based on the modeling rules identified in step 116. In one embodiment, the model generator is integrated with SPSS or some similar modeling software to generate a predictive model based on using Rest APIs. The Rest API allows a user to send requests (i.e., add predictive, update details of predictive rule) with information via http to the server. The predictive model can be used against unstructured and/or structured content to generate a predictive score. For example, patient data can be used to generate a predictive score for a CHF readmission.

After the predictive model has been created, it is examined whether there are any more sections in the document to be analyzed. If not, the process returns to step 110. If there are any further sections, the process returns to step 114 and continues as outlined above.

Use Example

To further illustrate the process described above, consider the following example, in which the following medical model is provided. Table 1 below indicates a point designation based on predictors for 8-year risk of Type 2 diabetes in middle-aged adults. Table 2 indicates an approximate percentage risk of Type 2 diabetes in middle-aged adults, based on the total points obtained in Table 1.

TABLE 1

Point designation based on predictors for 8-year risk of type 2 diabetes in middle-aged adults

| Predictor | Points |
|---|---|
| Fasting glucose level 100-126 mg/dL | 10 |
| BMI 25.0-29.9 | 2 |
| BMI >30.0 | 5 |
| HDL-C level <40 mg/dL in men or <50 mg/dL in women | 5 |
| Parental History of diabetes mellitus | 3 |
| Triglyceride level >150 mg/dL | 3 |
| Blood pressure >130/85 mmHG or receiving treatment | 2 |

TABLE 2

Given total points from Table 1, there is an approximate percentage risk for type 2 diabetes in middle-aged adults

| Total Points | 8-year risk, % |
|---|---|
| 10 or less | 3 or less |
| 11 | 4 |
| 12 | 4 |
| 13 | 5 |
| 14 | 6 |
| 15 | 7 |
| 16 | 9 |
| 17 | 11 |
| 18 | 13 |
| 19 | 15 |
| 20 | 18 |
| 21 | 21 |
| 22 | 25 |
| 23 | 29 |
| 24 | 33 |
| 25 or more | 35 or more |

When analyzing this data, the following dictionaries may be used, in one embodiment:
Medical Model Indicator Dictionary
   Risk Model
   Medical Model
   Risk
   Point Designation
   Risk Score
Age Dictionary
   Population of interest
   Age
   Age Range
Point Dictionary
   Total Points
   Points
Risk Value Dictionary
   Risk
   Percent
   Risk Score
Unit Dictionary
   Year
   Month
   Quarter
   Decade
   Century Predictor Dictionary
  Fasting glucose
  BMI
  HDL-C
  Parental history of diabetes mellitus
  Triglyceride
  Blood Pressure
  Receiving Treatment
Range Symbol Dictionary
  —
  to
Gender Dictionary
  Men
  Women
  Male
  Female Some examples of parsing rules that may be included when performing natural language processing the data in the above document, in accordance with one embodiment, are listed below:

Predictor Factor Rules
  Predictor dictionary followed by a number followed by a measurement.
  Predictor dictionary followed by mathematical sign followed by a number.
  Predictor dictionary followed by number followed by a range symbol followed by a number.
  These rules will identify range, measurement unit, conditional (i.e., gender) and points.
Multi Predictor Factor Rule
  Predictor Dictionary followed by the text 'and' followed by Predictor Dictionary.
Risk Value Rule
  Risk Value dictionary followed by %.
  Number followed by unit dictionary followed by Risk Value dictionary.
Risk Conversion Annotation Rule
  Points dictionary followed by Risk Value Rule.
Age Rules
  Age dictionary followed by a number followed by the text 'years'==>The number is set to the age minimum and age maximum feature annotations.
  Age dictionary followed by a number followed by range symbol followed by a number followed by the text 'years'=>The first number is set to the age minimum and the second number is set to age maximum.
  Number followed by the text 'to' followed by a number followed by the text 'years'==>The first number is set to the age minimum and the second number is set to age maximum feature annotations.
  Number followed by the text 'years'==>The number is set to the age minimum and age maximum feature annotations.

This Age analytic rule identifies the age or age range for patients in the model and in one embodiment, the system generates a Predictive Node Rule based on the age analytic rule. The Predictive Node Rule is an SPSS concept and represents a step in a process, similar to a block in a flow diagram. One or more rules can be implemented in a single SPSS node. Some examples of SPSS nodes include file input nodes (i.e., configure how to input data), data mining algorithm node (i.e., decision tree, clustering), etc. One example of a predictive node rule is:
  If age >70, then risk of heart disease is 45%
  If a table is followed by a medical model indicator annotation, then the table is parsed for column and row headers. Next the analytic engine parses the text. It reads the text token-by-token and row-by-row to determine the Predictive Model to be generated.

By applying the dictionaries and rules to Table 1 above, the following annotations are generated, in accordance with one embodiment:
Age Range Annotation: 45 to 64 years
  Age minimum annotation=45
  Age maximum annotation=64
  The system would generate a predictive model node rule:
Age>=45 and Age<=64
Predictor Factor Annotations:
  Fasting glucose (range feature =100-126, measurement=mg/dL, points=10)
  BMI (range feature=25.0-29.9, points=2)
  BMI (range feature='>30', points=5)
  HDL-C (range feature='<40', measurement=mg/dL, conditional=male, points=3)
  HDL-C (range feature='<50', measurement=mg/dL, conditional=female, points=3)
  Parental history of diabetes mellitus (points=3)
  Triglyceride (range feature='>150', measurement=mg/dL, points=3)
  Blood pressure (range feature='>130/85', measurement=mmHG, point=2)
  Receiving treatment (point=2)

The system can generate a predictive model node rule for each of these annotations by using the API of the predictive software, such as SPSS. The predictor factor annotation value combined with the range feature and measurement unit is used to generate the model rule. The points feature value is used to assign a number of points should the predictive model node criteria be met (e.g., age between 60 and 70, then assign 3 points). If there is no range feature value then a Boolean predictive model rule node is generated (e.g., male, then add 1 point to the risk). If the conditional feature value is set, then it is included in the predictive model node criteria.

Analyzing Table 2 generates data for the point to percent conversion. That is:
Risk Value Rule Annotation:
  8 year risk, %
Points Annotation:
  Total Points
  Since these annotations are in the table headers, the parser goes line-by-line and generates the Risk conversion annotation. For example:
Risk Conversion Annotation:
  Points=11
  Risk value=4

It should be noted that this is merely one exemplary implementation, and that the above concepts can be used in the context of many other products, such as the IBM Advanced Care Insights product, the IBM Watson Content Analytics product and the IBM SPSS Modeler product, all of which are available from International Business Machines Corporation of Armonk, N.Y. As the skilled person realizes, the above list of dictionaries and rules is not exclusive, and many other types of dictionaries and rules can also be used within this context.

Figure 2:
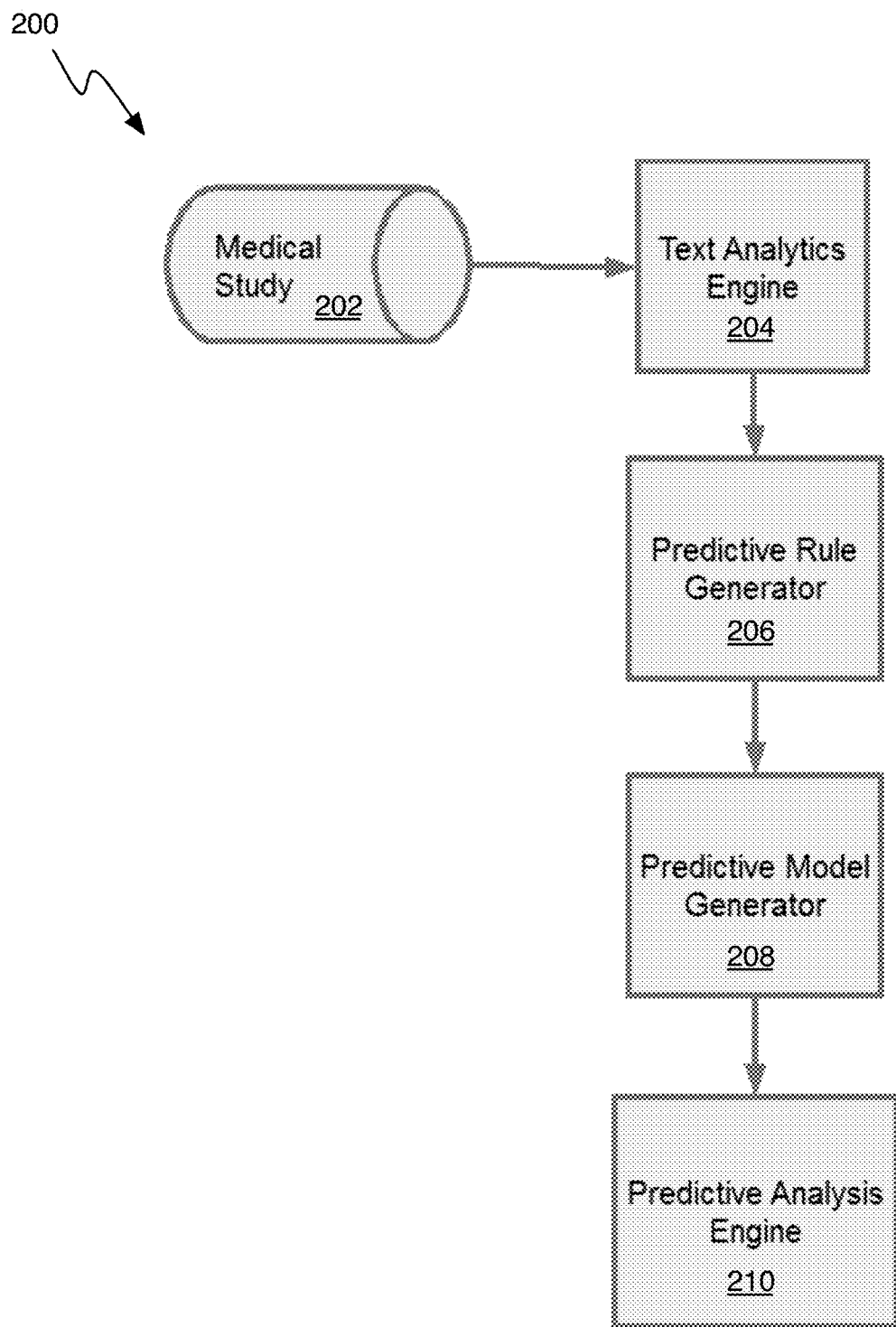
FIG. 2 is a block diagram showing a system for generating a predictive model based on medical model data, in accordance with one embodiment.

FIG. 2 shows a system (200), in accordance with one embodiment, for generating a predictive model. As can be seen in FIG. 2, the system (200) includes a text analytics engine (204), a predictive rule generator (206), a predictive model generator (208) and a predictive analysis engine (210). FIG. 2 also shows how the medical study data (202) is ingested into the system (200). In the illustrated embodiment, the text analytics engine (204) performs steps 102-112 of FIG. 1, the predictive rule generator (206) performs steps 114-116 of FIG. 1, the predictive model generator performs step 118 of FIG. 1, and once the predictive model has been generated, it can be used by the predictive analytics engine (210). The system (200) can be advantageously implemented on one or more computers and/or servers or on specialized computers/modules that perform each of the steps described in FIG. 1.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A computer-implemented method for text analysis of medical study data to extract predictive data, comprising:
   performing natural language processing on a document in a collection of documents to determine whether the document contains medical model data;
   in response to determining that the document contains medical model data, generating annotations for content relating to the medical model data in the document using section and modeling rule dictionaries;
   for a first section of the document, identifying one or more first medical modeling rules in the first section using the annotations, wherein a medical modeling rule of the first medical modeling rules is generated using a predictor factor annotation value, a range feature, and a measurement unit;
   generating a first medical model based on the annotations for the identified one or more first medical modeling rules and a certainty threshold;
   in response to the certainty threshold meeting a user setting, adding the first medical model to a predictive model;
   for a second section of the document, identifying one or more second medical modeling rules in the second section using the annotations;
   updating the predictive model based on the identified one or more second medical modeling rules and the certainty threshold; and
   using the predictive model against unstructured or structured content to generate a predictive score.

2. The method of claim 1, wherein the certainty threshold is configured by a user in a property file or through a user interface.

3. The method of claim 1, wherein the natural language processing uses a set of predetermined dictionaries and parsing rules to determine whether the document contains the medical model data.

\* \* \* \* \*